US00PP10204P

United States Patent [19]

Noodelijk

[11] Patent Number: Plant 10,204

[45] Date of Patent: Jan. 20, 1998

[54] CHRYSANTHEMUM PLANT NAMED 'REMIX'

[75] Inventor: Robert Noodelijk, Woubrugge, Netherlands

[73] Assignee: Chrysanthemum Breeders Association, N.V., Netherlands

[21] Appl. No.: 738,600

[22] Filed: Oct. 29, 1996

[51] Int. Cl.[6] ..... A01H 5/00

[52] U.S. Cl. ..... Plt./74.1

[58] Field of Search ..... Plt./74.1

*Primary Examiner*—Howard J. Locker

*Attorney, Agent, or Firm*—Parkhurst, Wendel & Burr, L.L.P.

[57] ABSTRACT

A new and distinct cultivar of chrysanthemum plant named 'Remix', bearing medium to large sized purple and white blooms with a yellow-green center and performance of 19–22 days.

2 Drawing Sheets

BACKGROUND OF THE INVENTION

The new plant of the present invention comprises a new and distinct cultivar of Chrysanthemum plant which is a cross of unknown *Chrysanthemum morifolium* parents. The new and distinct cultivar was a seedling resulting from the open pollination among groups of chrysanthemum cultivars maintained under the control of the inventor for breeding purposes. The new and distinct cultivar was discovered in a greenhouse in Ter Aar, Holland in 1988. The invention has been asexually reproduced by cuttings in greenhouses at Ter Aar, Holland. The new cultivar has been found to retain its distinctive characteristics through successive propagations.

SUMMARY OF THE INVENTION

The present invention is a new and distinct variety of Chrysanthemum of a medium to large sized bloom and purple and white color.

BRIEF DESCRIPTION OF THE DRAWINGS

The present invention of a new and distinct variety of Chrysanthemum is shown in the accompanying drawings, the color being as nearly true as possible with color photographs of this type.

DESCRIPTION OF THE INVENTION

Figure 1:
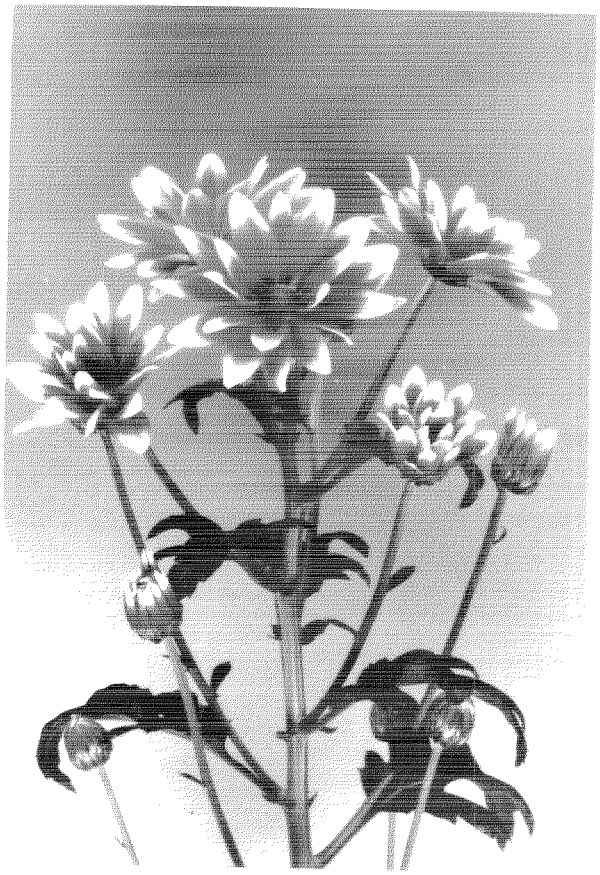
FIG. 1 shows the full bloom of the new cultivar.
Figure 2:
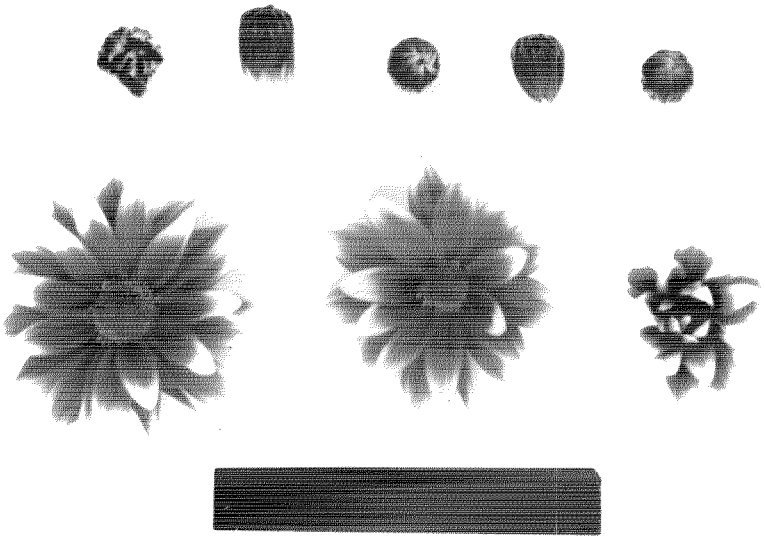
FIG. 2 shows the various stages of bloom of the new cultivar.
Figure 3:
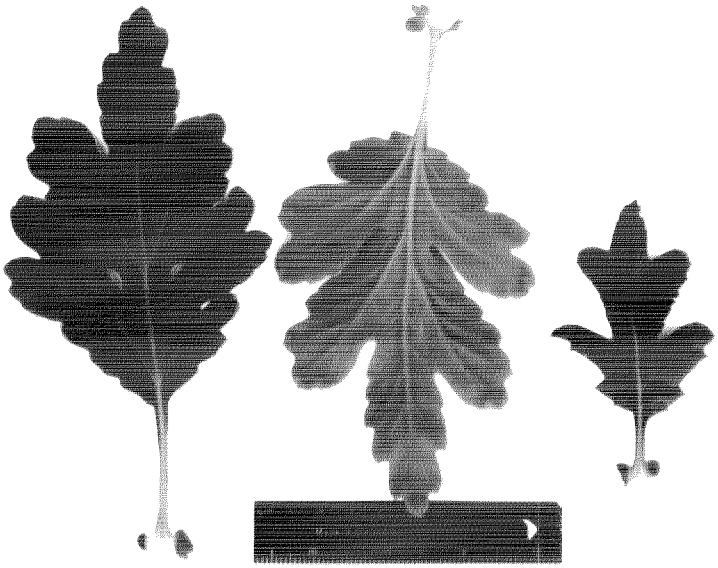
FIG. 3 shows foliage and petiole of the new cultivar.

This new variety of Chrysanthemum is of the botanical classification *Chrysanthemum morifolium*. When grown in the vicinity of Ter Aar, Holland, it has a response time of approximately 8 weeks. This new variety produces medium to large sized purple and white blooms with a green center having a 3 week performance (i.e., vase life of 19–22 days). This new variety of chrysanthemum has been found to retain its distinctive characteristics throughout successive propagations and may be planted under greenhouse conditions in Holland between weeks 2 and 32.

The following is a description of the plant and characteristics (color designations are from R.H.S. Color-Chart) that-distinguish it from related known varieties and its antecedents: The color designations are taken from the plant itself. Accordingly, any discrepancies between the color designations and the colors depicted in the photographs are due to photographic tolerances.

A comparison and botanical description of 'Remix' and related cultivar 'Yellow Remix' follows. 'Yellow Remix' is disclosed in copending application Ser. No. 8/739,453.

Botanical Classification

| CULTIVAR | REMIX | YELLOW REMIX |
|---|---|---|
| Bud | | |
| Size | large cross section ±1.3 cm height ±1.0 cm | large cross section ±1.3 cm height ±1.0 cm |
| Form | round and flat | round and flat |
| Outside Color | Red-Purple 61A | Greyed-Purple 187B tipped with yellow |
| Bloom | | |
| Size | Medium to large | Medium to large |
| Fully Expanded | 7–7½ cm | 7–7½ cm |
| Borne | Upper portion single flower per peduncle, lower portion plural flower per peduncle. | Upper portion single flower per peduncle, lower portion plural flower per peduncle. |
| Peduncle Lengths | Near the top ±8 cm Near the middle ±15 cm Near the bottom ±20 cm | Near the top ±8 cm Near the middle ±15 cm Near the bottom ±20 cm |
| Peduncle Lateral Shoot, Attachment | Medium | Medium |
| Peduncle Lateral Shoot, Angle | Large | Medium |
| Form | Single (daisy) | Single (daisy) |
| Performance | Good 19–22 days (18–20° C.) | Good 19–22 days (18–20° C.) |
| Color | | |
| Center of Flower | Immature: Yellow-Green 144A Mature: Yellow-Green 144B | Immature: Yellow-Green 144A Mature: Yellow-Green 144B |
| Base of Ray florets | Red-Purple 72B becoming White 155D at the tips. | Red 46A |
| Outer Ray florets | Red-Purple 72B becoming White 155D at the tips. | Red 46A becoming Yellow 6A at the tips |
| Inside of Ray florets | Red-Purple 72B becoming White 155D at the tips. | Red 46A becoming Yellow 6A at the tips |
| Reverse of Ray florets | White 155D strongly tinged with Red-Purple 72A, becoming whiter at the tips. | Yellow 6A with strong purple tints, near Red-Purple 59B, except at the tip. |
| Tonality from Distance | A purple and white daisy with a | A yellow and red daisy with a |

-continued

Botanical Classification

| CULTIVAR | REMIX | YELLOW REMIX |
|---|---|---|
| | green center | green center |
| | having some pollen | having some pollen |
| Discoloration | to Red-Purple 71D | to Red 45A becoming |
| | becoming White | Yellow 6A |
| | 155D at the tips. | at the tips |
| Pollen | Yellow-Orange 14A | Yellow-Orange 14A |
| Ray florets | | |
| Texture | Upperside smooth, | Upperside smooth, |
| | underside smooth. | underside smooth. |
| Number | 20–26 (two rows) | 20–26 (two rows) |
| Cross-section | flat (no keels) | flat, two keels |
| Arrangement | Imbricated | Imbricated |
| Persistence | Good, ray florets | Good, ray florets |
| | keep straight | keep straight |
| | or reflex | or reflex |
| | somewhat at the | somewhat at the |
| | edge at the | edge at the |
| | end of blooming. | end of blooming. |
| Fragrance | Typical chrysanthemum | Typical chrysanthemum |
| Disc Diameter | Medium (±1.5 cm) | Medium (±1.5 cm) |
| Reproductive Organs | | |
| Stamen | Yellow, thick ±4 | Yellow, thick ±4 |
| | mm in length | mm in length |
| Pollen | Appears | Appears |
| | fairly soon | fairly soon |
| Styles | green, thick | green, thick |
| Style Length | ±6 mm | ±6 mm |
| Stigmas | yellow | yellow |
| Stigma Width | ±2 mm | ±2 mm |
| Ovaries | Enclosed in calyx | Enclosed in calyx |
| Plant | | |
| Form | Spray mum meant | Spray mum meant |
| | for erect culture. | for erect culture. |
| | Herbaceous. | Herbaceous. |

-continued

Botanical Classification

| CULTIVAR | REMIX | YELLOW REMIX |
|---|---|---|
| Growth | Short to medium | Short to medium |
| Height | 100–125 cm | 100–125 cm |
| Stem Color | Yellow-Green 144A | Yellow-Green 144A |
| Stem Strength | Weak to medium | Weak to medium |
| Stem Brittleness | Absent | Absent |
| Stem Anthocyanin Coloration | Present | Present |
| Internodes | 2–2½ cm | 2–2½ cm |
| Flowering Response | 8 weeks | 8 weeks |
| Foliage | | |
| Color | Green 137A | Green 137A |
| Size | Length ±13 cm. | Length ±13 cm. |
| | Width ±10 cm. | Width ±9 cm. |
| Quantity | 20–26 | 20–26 |
| Shape | lobed, see photograph | lobed, see photograph |
| Texture | Upperside rough, | Upperside rough, |
| | underside smooth, | underside smooth, |
| | slightly hirsute. | slightly hirsute. |
| Ribs and Veins | Ribs well developed, | Ribs well developed, |
| | veins not so | veins not so |
| | developed | developed |
| Edge | Crenated | Crenated |
| Shape of Base | Round | Round |
| of Sinus Between Lateral Lobes | Round | Round |
| Margin of Sinus Between Lateral Lobes | Converging | Converging |
| Shape of Base | Truncate | Truncate |
| Apex | Mucronate | Mucronate |

I claim:

1. A new and distinct variety of Chrysanthemum plant as described and illustrated.

* * * * *